United States Patent [19]
Ichinohe et al.

[11] Patent Number: 5,817,852
[45] Date of Patent: Oct. 6, 1998

[54] DESULFURIZATION OF POLYSULFIDE SILANES

[75] Inventors: Shoji Ichinohe; Hideyoshi Yanagisawa, both of Gumma-ken, Japan

[73] Assignee: Shin-Etsu Chemical Co., Ltd., Tokyo, Japan

[21] Appl. No.: 933,974

[22] Filed: Sep. 19, 1997

[30] Foreign Application Priority Data

Nov. 29, 1996 [JP] Japan .................................. 8-334919

[51] Int. Cl.⁶ ........................................................ C07F 7/08
[52] U.S. Cl. .................................................... 556/427
[58] Field of Search ............................................. 556/427

[56] References Cited

U.S. PATENT DOCUMENTS

| | | |
|---|---|---|
| 3,873,489 | 3/1975 | Thurn et al. . |
| 3,997,356 | 12/1976 | Thurn et al. . |
| 4,076,550 | 2/1978 | Thurn et al. . |
| 5,663,395 | 9/1997 | Gobel et al. ............................. 556/427 |

FOREIGN PATENT DOCUMENTS 51-20208   6/1976   Japan .

*Primary Examiner*—Paul F. Shaver
*Attorney, Agent, or Firm*—Sughrue, Mion, Zinn, Macpeak & Seas, PLLC

[57] ABSTRACT

A polysulfide silane mixture is reacted with a phosphine or phosphite to produce a polysulfide silane mixture having a reduced content of high polysulfide silanes.

2 Claims, No Drawings

DESULFURIZATION OF POLYSULFIDE SILANES

BACKGROUND OF THE INVENTION

1. Field of the Invention

This invention relates to a method for desulfurizing polysulfide silanes and more particularly, to a method for desulfurizing polysulfide silanes to produce a polysulfide silane mixture having a smaller content of high polysulfide silanes and especially, an increased content of trisulfide and tetrasulfide silanes, and useful as a silane coupling agent for use in silica-blended rubber.

2. Prior Art

The contemporary demand to reduce the fuel consumption of automobiles requires to reduce the heat release of tire rubber compounds. From such a standpoint, attention was paid to silica-blended rubber compounds. JP-B 20208/1976, for example, discloses a reinforcing agent in the form of silica treated with a silane coupling agent. The silane coupling agent commonly used for this purpose is Si69 by Degussa, Inc. which is a mixture of polysulfide silanes of the structure:

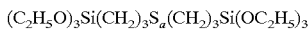

wherein letter a is an integer of 1 to 9. More specifically, this silane coupling agent is a mixture of polysulfide silanes wherein a ranges from 1 to 9. The average number of sulfur atoms is usually about 4. The content of high polysulfide silanes with a greater than 5 is relatively large.

Silane coupling agents of this type, however, are not fully reinforcing if the rubber mixing temperature is low and suffer from a problem of blister due to vaporization of ethanol. If hot mixing is effected at a temperature of higher than 150° C., the reinforcement effect is improved, but a polymer resulting from the silane coupling agent gels to increase the Mooney viscosity so that the rubber becomes difficult to work with in later steps.

Making investigations on silane coupling agents adapted for hot mixing, we have found that the content of high polysulfide silanes such as heptasulfide and hexasulfide silanes in polysulfide silanes must be reduced in order to avoid gelation of polymers.

However, if the composition of polysulfide silanes is altered simply through the following reaction scheme (A), then the overall distribution is shifted so that the content of disulfide silane having no coupling effect is increased.

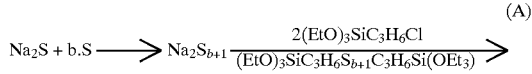

(A)

In scheme (A), Et is ethyl and b<3. There is a desire to have an effective means for selectively remove high polysulfide silanes.

SUMMARY OF THE INVENTION

Therefore, an object of the invention is to provide a method for desulfurizing polysulfide silanes so as to selectively remove high polysulfide silanes such as heptasulfide and hexasulfide silanes, thereby producing a sulfide silane mixture having a smaller content of high sulfide silanes, which when used in silica-blended rubber, restrains crosslinking reaction of polymers upon hot mixing at temperatures higher than 150° C., suppresses gelation of polymers, and exerts satisfactory coupling effect.

We have found that when a trivalent phosphorus compound, typically phosphine and phosphite is added to a mixture of polysulfide silanes of the following general formula (1) containing 1 to 9 sulfur atoms and having an average sulfur atom number in excess of 2, the trivalent phosphorus compound selectively reacts with high polysulfide silanes whereby sulfur is partially removed from these polysulfide silanes. As a result, there is obtained a mixture of polysulfide silanes of the following general formula (2) wherein the content of high polysulfide silanes such as heptasulfide and hexasulfide silanes is reduced. The thus obtained polysulfide silane mixture is useful as a silane coupling agent to be used in silica-blended rubber and restrains crosslinking reaction of polymers upon hot mixing at temperatures higher than 150° C. The invention is predicated on this finding.

Specifically, the present invention provides a method for desulfurizing polysulfide silanes, comprising the step of reacting a mixture of polysulfide silanes of the following general formula (1):

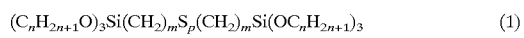

(1)

wherein letter n is an integer of 1 to 3, m is an integer of 1 to 9, and p representative of an average number of sulfur atoms is a positive number: p>2, with a trivalent phosphorus compound to reduce the content of high polysulfides in the polysulfide silane mixture, thereby yielding a mixture of polysulfide silanes of the following general formula (2):

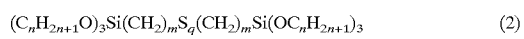

(2)

wherein letters n and m are as defined above, and q representative of an average number of sulfur atoms is a positive number: q<p, having a smaller content of high polysulfide silanes.

DETAILED DESCRIPTION OF THE INVENTION

The polysulfide silane mixture from which sulfur should be removed according to the invention is a mixture of polysulfide silanes of the following general formula (1):

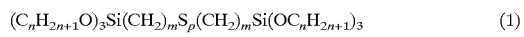

(1)

wherein letter n is an integer of 1 to 3, m is an integer of 1 to 9, and p representative of an average number of sulfur atoms is a positive number: p>2, preferably 2<p<9, especially 2<p<5.

This polysulfide silane mixture is a mixture of sulfide silanes having 1 to 9 sulfur atoms, especially 2 to 8 sulfur atoms. The polysulfide silane mixture used herein may be one obtained by conducting a process similar to the aforementioned scheme (A) and controlling reaction conditions such that the sulfur content may fall within the above-defined range of p.

According to the invention, the polysulfide silane mixture is reacted with a trivalent phosphorus compound. The trivalent phosphorus compounds used herein include phosphines such as $P(NR^1R^2)_3$ and $P(R^3)_3$ and phosphites such as $P(OR^4)_3$ and those represented by the following formula (3).

(3)

Herein, $R^1$ to $R^5$ are independently selected from hydrogen and substituted or unsubstituted monovalent hydrocarbon groups, preferably having 1 to 20 carbon atoms, such as alkyl, alkenyl, aryl, and aralkyl groups. Exemplary substituted monovalent hydrocarbon groups are halogenated ones. $R^6$ is a substituted or unsubstituted divalent hydrocarbon group, preferably an alkylene group, having 1 to 10, preferably 1 to 6 carbon atoms.

Among these phosphorus compounds, preferred phosphines are of the $P(R^3)_3$ type wherein $R^3$ is a group other than hydrogen. Preferred examples of the phosphine are given below.

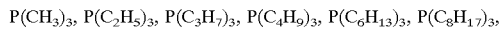

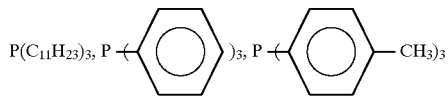

Preferred examples of the phosphite are given below.

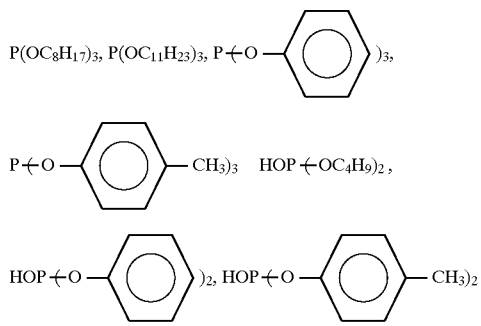

Also preferred are diphosphites as shown below.

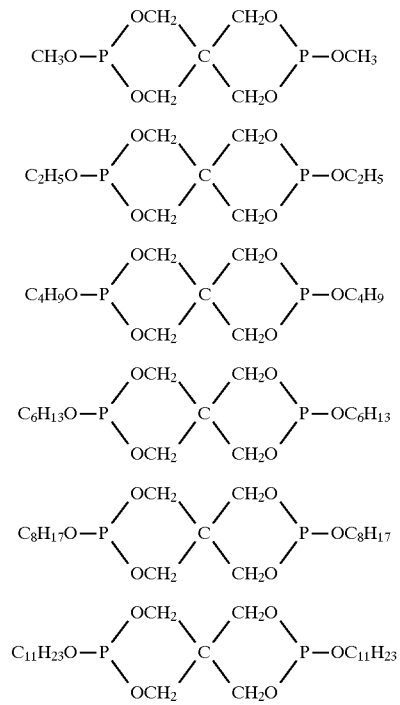

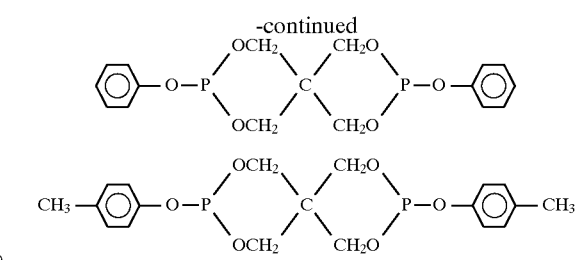

The reaction of the polysulfide silane mixture with the trivalent phosphorus compound is generally carried out at a temperature of −10° C. to 80° C., preferably 20° C. to 60° C.

Since this reaction is exothermic, the trivalent phosphorus compound is preferably added dropwise to the polysulfide silane for reaction to take place. A reaction time within 8 hours is satisfactory if the reaction temperature is 50° to 60° C. The solvent may be used or not. If used, the solvent is selected from conventional solvents including alcohol solvents such as ethanol, hydrocarbon solvents (aromatic and aliphatic), ester solvents, ether solvents, ketone solvents, and chlorinated solvents.

Sulfur-containing phosphorus compounds are formed as a result of desulfurization. They can be removed from the polysulfide silane mixture by vacuum distillation or filtration. Where it is desired to use the polysulfide silane mixture as a silane coupling agent for silica-blended rubber, especially vehicle tire rubber, the polysulfide silane mixture may be used without removing sulfur-containing phosphorus compounds because the sulfur-containing phosphorus compounds do not adversely affect tires' physical properties.

The molar ratio of the polysulfide silane mixture to the trivalent phosphorus compound on reaction varies with the average polysulfide length (the value of p) of the polysulfide silane mixture. Where the average number of polysulfide units is 2 to 4, the molar ratio of reactants may be 2 mol or less of the trivalent phosphorus compound to 1 mol of the polysulfide silane mixture. In the case of an average tetrasulfide silane, for example, it is preferred to use 0.5 to 2 mol of the trivalent phosphorus compound per mol of the tetrasulfide silane.

More particularly, when 0.5 mol of a phosphine or phosphite is reacted with 1 mol of a polysulfide silane $(C_2H_5O)_3SiC_3H_6S_pC_3H_6Si(OC_2H_5)_3$ wherein p=4, there is obtained a polysulfide silane wherein the average of polysulfide units is about 3.5. Tire-forming rubber having this polysulfide silane mixture blended therein is fairly acceptable with respect to hot mixing and contributes to the reduction of fuel consumption. When 1 to 1.5 mol of a phosphine or phosphite is reacted with 1 mol of the polysulfide silane of the above formula, there is obtained a polysulfide silane wherein the average of polysulfide units is about 2.5 to 3 which ensures a good balance of hot mixing and reduced fuel consumption. When 2 mol of a phosphine or phosphite is reacted with 1 mol of the polysulfide silane of the above formula, there is obtained a polysulfide silane which is satisfactory with respect to hot mixing and fairly contributes to the reduction of fuel consumption when blended in tire-forming rubber.

High polysulfide silanes such as pentasulfide silane can also be removed by reacting 1 mol of a polysulfide silane mixture having 2.5 to 3 polysulfide units on the average with 0.5 mol or less of a trivalent phosphorus compound. In this case, desulfurization by phosphines and phosphites takes place according to the following scheme.

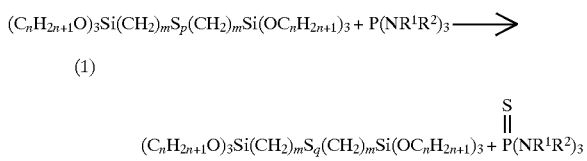

(1)

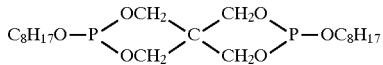

(2)

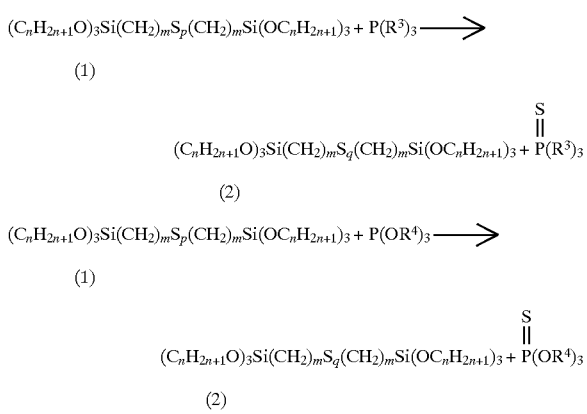

The following reaction takes place at the same time, but is not primary.

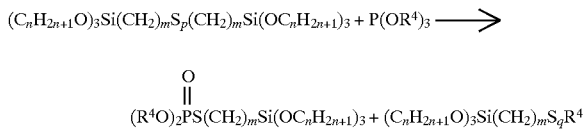

In these formulae, letters n, m and p are as defined above, and q representative of an average number of sulfur atoms is a positive number: $q<p$, preferably $2<q\leq 4$.

According to the desulfurization method of the invention, there is obtained a mixture of polysulfide silanes of formula (2). Since high polysulfide silanes have been converted into trisulfide silane and tetrasulfide silane, the mixture of polysulfide silanes of formula (2) has a large content of trisulfide silane and tetrasulfide silane useful as a silane coupling agent.

EXAMPLE

Examples of the invention are given below by way of illustration and not by way of limitation.

Example 1

A 1-liter flask was charged with 506 g (1 mol) of an average trisulfide silane (A) having a polysulfide distribution as shown in Table 1. With stirring, 49.9 g (0.3 mol) of triethyl phosphite was added dropwise from a dropping funnel to the flask over 2 hours. During this step, the internal temperature rose from 25° C. to 45° C. The contents were agitated for 3 hours at the temperature. Analysis by gas chromatography showed that the peak attributable to triethyl phosphite disappeared, indicating a progress of reaction. The thus obtained composition I was analyzed for polysulfide distribution by liquid chromatography. The results are shown in Table 1, indicating that high polysulfide units preferentially reacted.

Example 2

A composition II was obtained by carrying out reaction as in Example 1 except that the triethyl phosphite used in Example 1 was replaced by 67.8 g (0.15 mol) of a compound as shown below.

$$C_8H_{17}O-P\begin{array}{c}OCH_2\\OCH_2\end{array}C\begin{array}{c}CH_2O\\CH_2O\end{array}P-OC_8H_{17}$$

Example 3

A composition III was obtained by carrying out reaction as in Example 1 except that the triethyl phosphite used in Example 1 was replaced by 78.7 g (0.3 mol) of triphenyl phosphine.

Example 4

A composition IV was obtained by carrying out reaction as in Example 1 except that average trisulfide silane (A) used in Example 1 was replaced by 490 g (1 mol) of polysulfide silane (B) which had been reacted with sulfur so as to provide an average sulfide silane number of 2.5. The thus obtained composition IV was analyzed by liquid chromatography. The results are shown in Table 1.

It is noted that liquid chromatography was performed by means of Waters 600 system using an acetonitrile/water 9/1 (by weight) mixture as a solvent and UV radiation of 254 nm.

TABLE 1

Distribution of sulfide silanes $(C_2H_5O)_3SiC_3H_6S_xC_3H_6Si(OC_2H_5)_3$ in terms of liquid chromatography area (%)

| Polysulfide silane | x | | | | | | |
|---|---|---|---|---|---|---|---|
| | 2 | 3 | 4 | 5 | 6 | 7 | 8 |
| (A) | 6.3 | 31.2 | 27.8 | 20.4 | 10.4 | 3.9 | 0 |
| Composition I | 7.7 | 48.9 | 25.7 | 15.6 | 2.1 | 0 | 0 |
| Composition II | 8.0 | 46.5 | 26.3 | 15.8 | 3.4 | 0 | 0 |
| Composition III | 8.1 | 59.0 | 18.7 | 14.2 | 0 | 0 | 0 |
| (B) | 17.4 | 42.1 | 25.9 | 10.7 | 3.9 | 0 | 0 |
| Composition IV | 20.5 | 56.4 | 20.6 | 2.5 | 0 | 0 | 0 |

Example 5

A 1-liter flask was charged with 538 g (1 mol) of an average tetrasulfide silane (C) having a polysulfide distribution as shown in Table 2. With stirring, 83.1 g (0.5 mol) of triethyl phosphite was added dropwise from a dropping funnel to the flask over 2 hours. During this step, the internal temperature rose from 25° C. to 50° C. The contents were agitated for 3 hours at the temperature. Analysis by gas chromatography showed that the peak attributable to triethyl phosphite disappeared, indicating a progress of reaction. The thus obtained composition V was analyzed for polysulfide distribution by liquid chromatography. The results are shown in Table 2, indicating that high polysulfide units preferentially reacted.

Example 6

A composition VI was obtained by carrying out reaction as in Example 5 except that 166.2 g (1 mol) of triethyl phosphite as in Example 5 was added dropwise over 2 hours. During this step, the flask was cooled with water so as to maintain the internal temperature below 50° C. The reaction mixture was heated at 40° to 50° C. and stirred for 3 hours. The composition VI was analyzed for polysulfide distribution by liquid chromatography.

Example 7

A composition VII was obtained by carrying out reaction as in Example 6 except that 226 g (0.5 mol) of a compound shown below was used instead of the triethyl phosphite in Example 6. The composition VII was analyzed for polysulfide distribution by liquid chromatography.

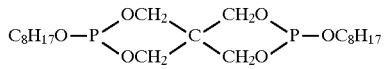

Example 8

A composition VIII was obtained by carrying out reaction as in Example 6 except that 262.3 g (1 mol) of triphenyl phosphine was used instead of the triethyl phosphite in Example 6. The composition VIII was analyzed for polysulfide distribution by liquid chromatography.

TABLE 2

Distribution of sulfide silanes $(C_2H_5O)_3SiC_3H_6S_xC_3H_6Si(OC_2H_5)_3$ in terms of liquid chromatography area (%)

| Sample | x=2 | 3 | 4 | 5 | 6 | 7 | 8 |
|---|---|---|---|---|---|---|---|
| (C) | 2.6 | 16.0 | 23.7 | 24.8 | 18.6 | 10.4 | 3.9 |
| Composition V | 5.0 | 29.9 | 43.1 | 16.9 | 5.1 | 0 | 0 |
| Composition VI | 11.1 | 62.8 | 26.1 | 0 | 0 | 0 | 0 |
| Composition VII | 12.7 | 58.2 | 28.3 | 0.8 | 0 | 0 | 0 |
| Composition VIII | 8.3 | 64.1 | 27.6 | 0 | 0 | 0 | 0 |

There has been described a method for desulfurizing polysulfide silanes by reacting the polysulfide silanes with a trivalent phosphorus compound, which ensures production of a polysulfide silane mixture having a reduced content of high polysulfide silanes.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for desulfurizing polysulfide silanes, comprising the step of reacting a mixture of polysulfide silanes of the following general formula (1):

$$(C_nH_{2n+1}O)_3Si(CH_2)_mS_p(CH_2)_mSi(OC_nH_{2n+1})_3 \qquad (1)$$

wherein letter n is an integer of 1 to 3, m is an integer of 1 to 9, and p representative of an average number of sulfur atoms is a positive number: p>2, with a trivalent phosphorus compound of the formula:

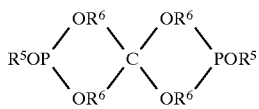

wherein $R^5$ is a hydrogen or substituted or unsubstituted monovalent hydrocarbon group, and $R^6$ is a substituted or unsubstituted divalent hydrocarbon group, to reduce the content of high polysulfides in the polysulfide silane mixture, thereby yielding a mixture of polysulfide silanes of the following general formula (2):

$$(C_nH_{2n+1}O)_3Si(CH_2)_mS_q(CH_2)_mSi(OC_nH_{2n+1})_3 \qquad (2)$$

wherein letters n and m are as defined above, and q representative of an average number of sulfur atoms is a positive number: q<p, having a smaller content of high polysulfide silanes.

2. The method of claim 1 wherein the reaction of the mixture of polysulfide silanes of formula (1) with the trivalent phosphorus compound is carried out at a temperature of −10° C. to 80° C.

* * * * *